US006251595B1

(12) United States Patent
Gordon et al.

(10) Patent No.: US 6,251,595 B1
(45) Date of Patent: Jun. 26, 2001

(54) METHODS AND DEVICES FOR CARRYING OUT CHEMICAL REACTIONS

(75) Inventors: Gary B. Gordon, Saratoga; Douglas J. Dellinger, Sunnyvale, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/100,152

(22) Filed: Jun. 18, 1998

(51) Int. Cl.[7] .......................... C12Q 1/68; G01N 33/543; G01N 25/18; G01N 33/553; B32B 5/02
(52) U.S. Cl. ............................. 435/6; 204/400; 422/50; 422/68.1; 422/131; 422/186; 427/2.13; 435/7.1; 435/91.1; 435/DIG. 49; 436/501; 436/518; 436/525; 436/149
(58) Field of Search .......................... 422/68.1, 50, 131, 422/186; 204/400; 435/6, 7.1, 91.1; 436/501, 518, 149, 525; 427/2.13

(56) References Cited

U.S. PATENT DOCUMENTS

| | | | |
|---|---|---|---|
| 3,976,864 | * 8/1976 | Gordon et al. | ........................ 235/153 |
| 4,832,759 | 5/1989 | Curtis et al. . | |
| 5,180,480 | 1/1993 | Manz . | |
| 5,231,427 | * 7/1993 | Ohashi | ................................. 346/155 |
| 5,427,663 | 6/1995 | Austin et al. . | |
| 5,445,934 | 8/1995 | Fodor et al. . | |
| 5,474,796 | 12/1995 | Brennan . | |
| 5,582,701 | 12/1996 | Geis et al. . | |
| 5,605,662 | 2/1997 | Heller et al. . | |
| 5,632,957 | 5/1997 | Heller et al. . | |
| 5,653,939 | 8/1997 | Hollis et al. . | |
| 5,667,667 | 9/1997 | Southern . | |
| 5,728,532 | 3/1998 | Ackley . | |
| 5,965,452 | * 10/1999 | Kovacs | ................................. 436/149 |
| 6,021,172 | * 2/2000 | Fossum et al. | ........................ 377/60 |

FOREIGN PATENT DOCUMENTS

| | | |
|---|---|---|
| WO 95/25116 | 9/1995 | (WO) . |
| WO 95/01836 | 1/1996 | (WO) . |
| WO 96/07917 | 3/1996 | (WO) . |
| WO 97/12030 | 4/1997 | (WO) . |
| WO 98/01758 | 1/1998 | (WO) . |

* cited by examiner

*Primary Examiner*—Jyothsna Venkat
*Assistant Examiner*—Maurie E. Garcia

(57) ABSTRACT

Methods and devices are disclosed for carrying out multiple chemical reactions. A plurality of electrodes supported by a semiconductor substrate is brought into proximity with a reaction medium, which comprises reagents for carrying out the chemical reactions. An item of numerical data is sent to storage means in each of a plurality of cells within the semiconductor substrate by means of a data bus. The item of numerical data is representative of an electric signal. An address is sent to address decoders in communication with the storage means. As a result, the item of numerical data is stored in the storage means. Electric signals are selectively applied to each of the electrodes by means of a plurality of digital analog converters, each electrically coupled to a respective electrode. Each of the digital analog converters is associated with a respective cell. In this way, a chemical reaction takes place proximal to and in response to the field at the electrodes to which the electric signals are selectively applied. A particular feature of the present invention is that the medium may be non-aqueous.

26 Claims, 3 Drawing Sheets

METHODS AND DEVICES FOR CARRYING OUT CHEMICAL REACTIONS

BACKGROUND OF THE INVENTION

1. Field of the Invention

This invention relates to the field of bioscience in which arrays of oligonucleotide probes, fabricated or deposited on a surface, are used to identify DNA sequences in cell matter. The present invention has a wide range of application for synthesis of arrays for conducting cell study, for diagnosing disease, identifying gene expression, monitoring drug response, determination of viral load, identifying genetic polymorphisms, and the like.

Significant morbidity and mortality are associated with infectious diseases and genetically inherited disorders. More rapid and accurate diagnostic methods are required for better monitoring and treatment of these conditions. Molecular methods using DNA probes, nucleic acid hybridization and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double-stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the development of methods for their incorporation into DNA and RNA has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fumgi, and viruses.

The application of nucleic acid hybridization as a diagnostic tool in clinical medicine is limited due to the cost and effort associated with the development of sufficiently sensitive and specific methods for detecting potentially low concentrations of disease-related DNA or RNA present in the complex mixture of nucleic acid sequences found in patient samples.

One method for detecting specific nucleic acid sequences generally involves immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty eight hours. After the above time period, the solid support is washed several times at a controlled temperature to remove unhybridized probe. The support is then dried and the hybridized material is detected by autoradiography or by spectrometric methods. When very low concentrations must be detected, the above method is slow and labor intensive, and nonisotopic labels that are less readily detected than radiolabels are frequently not suitable. The above time period may be shortened by employing techniques such as electrophoresis, which allows detection of specific nucleic acid sequences in a relatively shorter time of about 10 minutes to one hour.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Other methods for amplifying nucleic acids have also been developed. These methods include single primer amplification, ligase chain reaction (LCR), transcription-mediated amplification methods including 3SR and NASBA, the Q-beta-replicase method, the rolling circle amplification, and so forth. Regardless of the amplification used, the amplified product must be detected.

One method for detecting nucleic acids is to employ nucleic acid probes that have sequences complementary to sequences in the target nucleic acid. A nucleic acid probe may be, or may be capable of being, labeled with a reporter group or may be, or may be capable of becoming, bound to a support. Detection of signal depends upon the nature of the label or reporter group. Usually, the probe is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. Commonly, binding of the probes to the target is detected by means of a label incorporated into the probe. Alternatively, the probe may be unlabeled and the target nucleic acid labeled. Binding can be detected by separating the bound probe or target from the free probe or target and detecting the label. In one approach, a sandwich is formed comprised of one probe, which may be labeled, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target, allowing the target to hybridize to a surface-bound probe, washing away the unbound target and detecting the labeled target that remains.

Direct detection of labeled target hybridized to surface-bound probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

In one approach, cell matter is lysed, to release its DNA as fragments, which are then separated out by electrophoresis or other means, and then tagged with a fluorescent or other label. The resulting DNA mix is exposed to an array of oligonucleotide probes, whereupon selective attachment to matching probe sites takes place. The array is then washed and imaged so as to reveal for analysis and interpretation the sites where attachment occurred.

The goal of array fabrication is to produce a matrix of the order of 10,000 probe sites or more in an area several to tens of millimeters on a side. Each oligonucleotide probe has a length typically in the 10 to 40 base pair length. Many methods have been put forth for fabricating such arrays. In one approach the oligonucleotide probes are spotted on a suitable surface to produce an array. For this purpose, pre-synthesized probes are employed. In another approach a substrate is prepared upon which is located microdrop-sized loci at which chemical compounds are synthesized or diagnostic tests are conducted. The loci are formed by applying microdrops from which a microdrop is pulse-fed onto the surface of the substrate.

In another approach, arrays are fabricated in situ, adding one base pair at a time to a primer site. Affymetrix, for example, uses photolithography to uncover sites, which are then exposed and reacted with one of the four base pair phosphoramidites. In photolithography the surface is first coated with a light-sensitive resist, exposed through a mask and the pattern is revealed by dissolving away the exposed or the unexposed resist and, subsequently, a surface layer. A separate mask must be made for each pattern, which may involve four patterns for each base pair in the length of the probe. Much overhead is involved in preparing the masks for photolithography, which may number 80 for probes of length 20, thus rendering this technique best suited for very high volume production. There are also problems in controlling the etching reaction and in registering masks between each step.

Another in situ method employs inkjet printing technology to dispense the appropriate phosphoramidite onto the individual probe sites. For example, see U.S. Pat. No. 5,700,637 and PCT WO 95/25116.

Another method involves electrochemically patterning a surface. An electrolyte overlying the surface and an array of electrodes adjacent to the surface and in contact with the electrolyte is provided. The potential of one or more electrodes of the array is altered so as to deposit or remove or chemically modify a substance on the surface adjacent the electrode. Several such treatments may be performed in sequence using different electrodes of the array. The method may be used for step-wise chemical synthesis of, for example, oligonucleotides tethered to the surface.

In a similar approach a self-addressable, self-assembling microelectronic device is used to carry out and control multi-step and multiplex molecular biological reactions, such as biopolymer synthesis, nucleic acid hybridization, antibody-antigen reaction, and diagnostics, in microscopic formats. The device electronically can control the transport and attachment of specific binding entities and other reactants to specific microlocations.

Array plates have been discussed where a glass support surface is coated with a positive or negative photoresist substance and then exposed to light and developed to create a patterned region of a first exposed surface and a photoresist coated surface on the support. The first exposed surface is reacted with a fluoroalkylsilane to form a stable fluoroalkylsiloxane hydrophobic matrix on the first exposed surface. The photoresist coat on the surface is removed so as to form a second exposed surface, which is reacted with a hydroxy- or aminoalkylsilane so as to convert the second exposed surface to a derivatized hydrophilic binding site region and thus form the array plate.

In another approach a biological electrode array is used. Each electrode in the array is coupled to a respective sample-and-hold circuit. The electrodes and sample-and-hold circuits are integral and form an array within a single semiconductor chip, such that each sample-and-hold circuit may be loaded with a predefined voltage provided by a single, time-shared digital-to-analog converter. All of the sample-and-hold may be accessed through a multiplexer that may scan through some or all of the electrode locations. Each sample-and-hold circuit may comprise a capacitor and one or more transistor switches, which, when closed, provide electrical communication between the capacitor and a source line formed in the matrix.

The known techniques are not without limitations, however. The photolithographic approach is time consuming, and thus expensive and, due to its chemical complexity, starts to introduce errors as the probe lengths grow much beyond ten base pairs. While the inkjet method offers better probe fidelity, its spot nature also slows down fabrication, and, thus, it is best-suited for lower volume array fabrication. Also, there is a potential problem with the chemical compatibility of reactive nucleotide intermediates with inkjet printing technology and the reproducibility of spot to spot registration.

The above-mentioned biological electrode array may be limited because of the requirements of the IC fabrication required to prepare the chips. According to known IC procedures, the chips must be electrically powered during the fabrication process resulting in potential generation of noise because of the continual refresh involved. Furthermore, the chips are individually reacted chemically so as to build the desired chemical structure at each site. The drawback of this approach is the expense of chemically programming the devices either individually or in small groups.

2. Description of the Related Art

PCT application WO 98/01758 (Kovacs) discloses a multiplexed active biologic array.

U.S. Pat. No. 5,605,662 (Heller, et al.) (Heller 1)) discloses active programmable electronic devices for molecular biological analysis and diagnostics. A corresponding PCT application is WO 95/12808. The devices and systems are self-addressable, self-assembling and microelectronic.

U.S. Pat. No. 5,632,957 (Heller, et al.) (Heller 2), and corresponding PCT application WO 95/01836, discuss molecular biological diagnostic systems including electrodes. The devices and systems are self-addressable, self-assembling and microelectronic.

Heller, et al., (Heller 3) disclose apparatus and methods for active programmable matrix devices in PCT application, WO 97/12030.

Heller, et al., (Heller 4) disclose an automated molecular biological diagnostic system in PCT application, WO 96/07917.

U.S. Pat. No. 5,667,667 (Southern) discloses electrochemical treatment of surfaces.

U.S. Pat. No. 5,180,480 (Manz) discusses an apparatus for the preparation of samples especially for analytical purposes.

Austin, et al., (Austin, U.S. Pat. No. 5,427,663) disclose microlithographic array for macromolecule and cell fractionation.

U.S. Pat. No. 5,582,701 (Geis, et al.) discusses an ionic liquid-channel charge-coupled device.

Hollis, et al., (Hollis, U.S. Pat. No. 5,653,939) disclose optical and electrical methods and apparatus for molecule detection.

U.S. Pat. No. 4,832,759 (Curtis, et al.) discloses the location of biological cells in a predetermined spatial disposition relative to each other on a solid non-biological substrate.

An electrode configuration for matrix addressing of a molecular detection device is discussed by Ackley in U.S. Pat. No. 5,728,532.

PCT WO 95/25116 (Baldeschwieler, et al.) discloses a method and apparatus for performing multiple sequential reactions on a matrix.

U.S. Pat. No. 5,474,796 (Brennan) discloses a method for making array plates.

U.S. Pat. No. 5,445,934 (Fodor, et al.) discusses an array of oligonucleotides on a solid substrate.

SUMMARY OF THE INVENTION

One embodiment of the present invention is a method for carrying out multiple chemical reactions. A plurality of electrodes supported by a semiconductor substrate is brought into proximity with a reaction medium, which comprises reagents for carrying out the chemical reactions. An item of numerical data is sent to storage means in each of a plurality of cells within the semiconductor substrate by means of a data bus. The item of numerical data is representative of an electric signal. An address is sent to address decoders in communication with the storage means. As a result, the item of numerical data is stored in the storage means. Electric signals are selectively applied to of the electrodes. In this way, a chemical reaction takes place proximal to and in response to the field at the electrodes to which the electric signals are selectively applied. A particular feature of the present invention is that the medium may be non-aqueous. In a particular embodiment a plurality of analog buses are employed and the item of numerical data identifies which analog bus connects to said electrode.

Another aspect of the present invention is a method for carrying out multiple chemical reactions. A device is brought into proximity with a reaction medium, which comprises reagents for carrying out the chemical reactions. The device comprises (i) a semiconductor substrate, (ii) a plurality of electrodes supported by the semiconductor substrate, (iii) a plurality of cells within the semiconductor substrate, (iv) a plurality of digital analog converters, each electrically coupled to a respective electrode and each being associated with a respective cell, (v) address decoders in communication with each of the cells, (vi) a data bus for delivering binary numerical data to each of the cells, (vii) address buses for delivering addresses to the address decoders, and (viii) storage means in each of the cell for storing the numerical data, the storage means being in communication with the digital analog converter in the cell. Binary numerical data is sent to the storage means of each of the cells by means of the data bus. The binary numerical data is representative of an electric signal. Addresses are sent to the address decoders whereby the binary numerical data is stored in the storage means and electric signals are selectively applied to each of the electrodes by means of the digital analog converters. A chemical reaction takes place proximal to and in response to the field at the electrodes.

Another aspect of the present invention is a device comprising (a) a semiconductor substrate, (b) at least one surface for carrying out a chemical reaction, (c) an electrode adjacent the surface and supported by the semiconductor substrate, (d) a cell within the semiconductor substrate, (e) a digital analog converter to which the electrode is electrically coupled, the digital analog converter being associated with the cell, (f) an address decoder in communication with the cell, (g) a data bus for delivering an item of numerical data to the cell, (g) an address bus for delivering an address to the address decoder, and (h) storage means in the cell for storing the item of numerical data, the storage means being in communication with the digital analog converter. In a further aspect of the present invention the device has a plurality of electrodes supported by the semiconductor substrate and a plurality of cells within the semiconductor substrate, a plurality of digital analog converters, each electrically coupled to a respective electrode and each being associated with a respective cell, address decoders in communication with each of the cells, a data bus for delivering an item of numerical data to each of the cells, address buses for delivering addresses to the address decoders, and storage means in each of the cells for storing the item of numerical data. In one embodiment the device further comprises a plurality of analog buses.

Another aspect of the present invention is a chip for electronically addressing a matrix of sites, to each of which may be directed a chemical reaction. The chip comprises (a) a semiconductor substrate, (b) a matrix of electronic circuit cells fabricated within the semiconductor substrate, (c) address decoders for activating a cell in response to an address applied to the chip, (d) a data bus for delivering binary numerical data to the cells, (e) storage means in each of the cells for storing binary numerical data from the data bus when activated by addresses decoded by the address decoders, (f) digital to-analog conversion means in each cell for converting binary numerical data into an electrical signal, (g) an electrode plate connected to each of the digital-to-analog conversion means. Electrical signals representative of the binary numerical data are selectively applied to each of the electrode plates for the purpose of inducing, when the device is placed proximal to a chemical medium, selective chemical activity according to the binary numerical data provided.

Another aspect of the present invention is a method for carrying out multiple chemical reactions. A plurality of electrodes supported by a semiconductor substrate is brought into proximity with a reaction medium, which comprises reagents for carrying out the chemical reactions. An item of numerical data is sent to storage means in each of a plurality of cells within the semiconductor substrate by means of a data bus. The item of numerical data is representative of an electric signal. An address is sent to address decoders in communication with the storage means and, as a result, the item of numerical data is stored in the storage means and electric signals are selectively applied to each of the electrodes by means of a plurality of digital analog converters. Each of the converters is electrically coupled to a respective electrode and each is associated with a respective cell. A chemical moiety proximal to the electrode is selectively activated for reaction with a reagent in the reaction medium. The selective activation is in response to the field at the electrodes to which the electric signals are selectively applied.

Another aspect of the present invention is a method of fabricating a plurality of individual chips, each for electronically addressing a matrix of sites, each site to which may be directed a chemical reaction. A plurality of such individual chips is prepared on a single silicon substrate, which is severed into said individual chips.

DEFINITIONS

Figure 1:
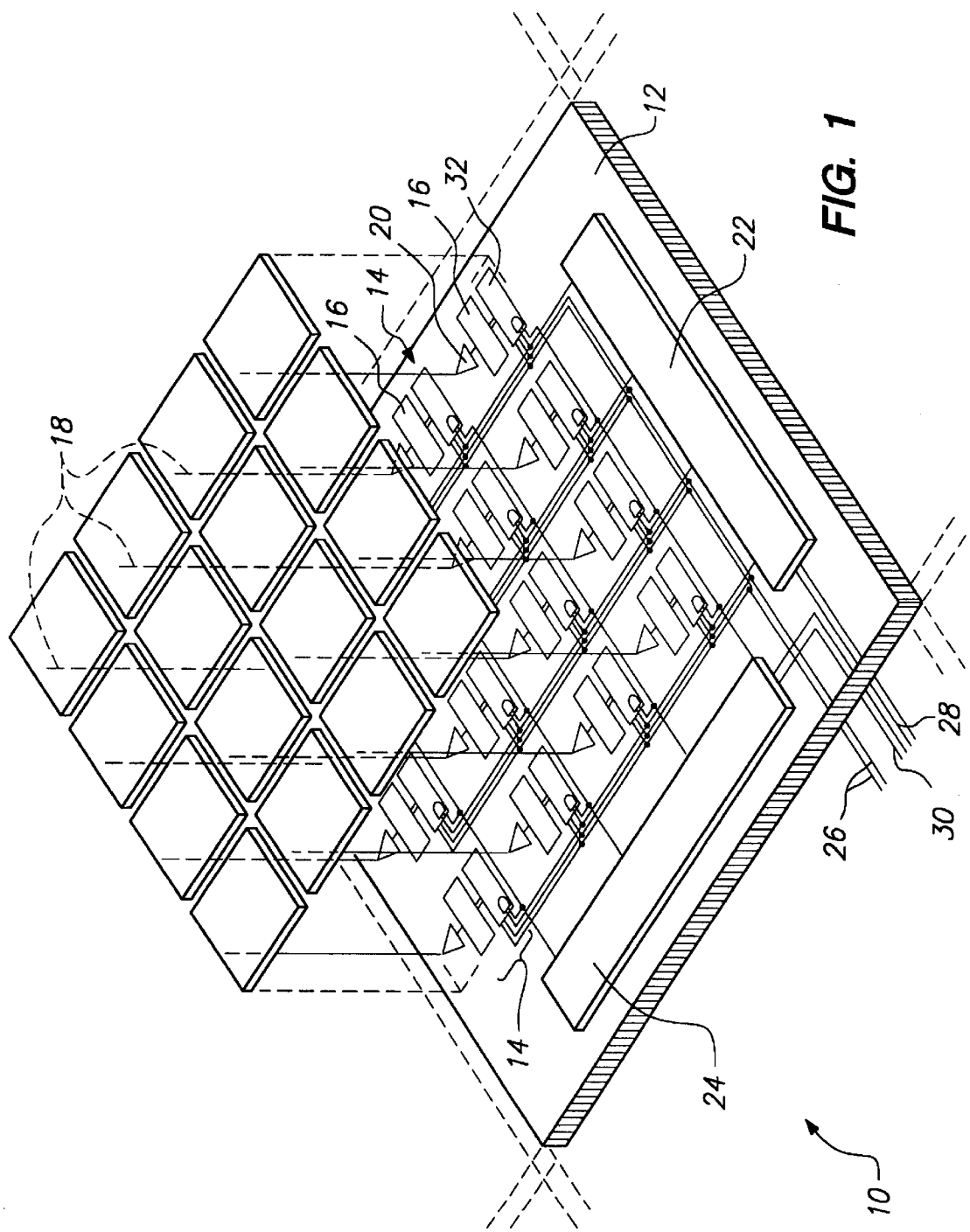
FIG. 1 is a schematic diagram depicting a device in accordance with the present invention.

Before proceeding further with a description of the specific embodiments of the present invention, a number of terms will be defined.

Polynucleotide—a compound or composition that is a polymeric nucleotide or nucleic acid polymer. The polynucleotide may be a natural compound or a synthetic compound. In the context of an assay, the polynucleotide is often referred to as a polynucleotide analyte. The polynucleotide can have from about 2 to 5,000,000 or more nucleotides. The larger polynucleotides are generally found in the natural state. In an isolated state the polynucleotide can have about 2 to 50,000 or more nucleotides, usually about 10 to 20,000 nucleotides, more frequently 100 to 10,000 nucleotides. It is thus obvious that isolation of a polynucleotide from the natural state often results in fragmentation. The polynucleotides include nucleic acids, and fragments thereof, from any source in purified or unpurified form including DNA (dsDNA and ssDNA) and RNA, including tRNA, MRNA, rRNA, mitochondrial DNA and RNA, chloroplast DNA and RNA, DNA/RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

The polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, dsDNA can be heated at 90 to 100° C. for a period of about 1 to 10 minutes to produce denatured material.

Target nucleotide sequence—a sequence of nucleotides to be identified, usually existing within a portion or all of a polynucleotide, usually a polynucleotide analyte. The identity of the target nucleotide sequence generally is known to an extent sufficient to allow preparation of various sequences hybridizable with the target nucleotide sequence and of oligonucleotides, such as probes and primers, and other molecules necessary for conducting methods in accordance with the present invention, an amplification of the target polynucleotide, and so forth.

The target sequence usually contains from about 30 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 10 to 100 nucleotides, more preferably, 20 to 50 nucleotides, and usually 10 to 30 nucleotides, more preferably, 15 to 30 nucleotides.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates.

Nucleotide—a base-sugar-phosphate combination that is the monomeric unit of nucleic acid polymers, i.e., DNA and RNA. The term "nucleotide" as used herein includes modified nucleotides as defined below.

DNA—deoxyribonucleic acid.

RNA—ribonucleic acid.

Modified nucleotide—a unit in a nucleic acid polymer that contains a modified base, sugar or phosphate group. The modified nucleotide can be produced by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophor-labeled, and the like and also include phosphorothioate, ring atom modified derivatives, and so forth.

Nucleoside—is a base-sugar combination or a nucleotide lacking a phosphate moiety.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, adding a surfactant, and the like.

Homologous or substantially identical polynucleotides— In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G/U or U/G base pairs.

Support or surface—a porous or non-porous water insoluble material. The surface can have any one of a number of shapes, such as strip, plate, disk, rod, particle, including bead, and the like. The support can be hydrophilic or capable of being rendered hydrophilic and includes inorganic powders such as glass, silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of oligonucleotides to a support or surface may be accomplished by well-known techniques, commonly available in the literature. See, for example, A. C. Pease, et al., Proc. Nat. Acad. Sci. USA, 91:5022–5026 (1994).

Label—a member of a signal producing system. Usually the label is part of a target nucleotide sequence or an oligonucleotide probe, either being conjugated thereto or otherwise bound thereto or associated therewith. The label is capable of being detected directly or indirectly. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used.

The reporter molecule can be isotopic or nonisotopic, usually non isotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like.

Signal Producing System—the signal producing system may have one or more components, at least one component being the label. The signal producing system generates a signal that relates to the presence or amount of a target polynucleotide in a medium. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like.

DETAILED DESCRIPTION OF THE INVENTION

In its broadest application the present invention is directed to methods for carrying out multiple chemical reactions. Any chemical reaction that may be conducted electrochemically can be conducted in accordance with the present invention. In one aspect of the present invention the reagents employed are those whose movement to a point of reaction may be controlled by application of electric fields and, thus, are electrically responsive. The reagent may be electrically responsive by virtue of having a charge either inherently or by virtue of introduction into the reagent of a group that creates a charge or a polarity in the reagent. Examples of inherently charged molecules are those having a positive or negative charge such as cationic molecules, anionic molecules, and the like. A group that imparts a charge to the molecule may be introduced to render the molecule electrically responsive. Such groups may be introduced into a molecule by methods that are well-known in the art. For example, in the context of synthesis of oligonucleotides, such a group may be introduced into the monomeric nucleoside reagent. Examples of such a group are groups that contain formal positive charges such as a quaternary ammonium ion. Also included are those groups that may be converted to one having a positive such as an amine-containing group that may be converted to a quaternary ammonium form by well-known methods. Such groups include, by way of illustration and not limitation, O-4 and O-6 protecting groups such as, for example, exocyclic amine protecting groups for A, C or G and O-4 protecting groups for T, (see, for example, Tanimura, et al., *Chemistry Letters* (1987) 1057–1060), phosphodiester groups, activated phosphorus groups such as, for example, Lewis acids in phosphotriester groups (see, e.g., Michelson, et al., *J. Chem. Soc.*

(Part 3) (1955) 2632–2638), H-phosphonate groups, trityl groups incorporating a quaternary ammonium form (see, e.g., Reddy, Tetrahedron Letters (1987) 28:23–26), primary amine-containing groups that may be converted to a tertiary amine by well-known approaches such as treatment with methyl iodide, phosphoramidite groups (see, e.g., Matteucci, Tetrahedron Letters, 24:3171–3175) and so forth. With respect to phosphoramidite groups, a tetrazole exchange product in protonated form is an active intermediate. Such groups identified above may be introduced into a molecule by methods that are well-known in the art, which are discussed in the references mentioned above.

Examples of groups that contain formal negative charges are carboxylic acid anions, sulfonic acid anions and the like. Such groups may be introduced into a molecule by methods that are well-known in the art.

In another aspect the reagents are reactive with reactive species generated at a site by virtue of the application of an electric field adjacent to the site. Exemplary of such reactive species are nucleophiles, electrophiles, acids, bases, and the like.

Particular examples of the above include generation of anions by removal of hydrogen from a hydroxyl group, generation of acids for removal of protecting groups and so forth. The above reactions may be carried out by approaches that are wellknown in the art.

In one particular approach an acid may be generated in the area adjacent a selected electrode whereas in the general buffered medium employed the acid is in the form of an acid salt. For example, in the perchloric acid deprotection of trityl protecting groups, a buffered medium may be employed so that the general population of perchloric acid molecules is in the form of a salt. However, in the area of the electrical field generated at a selected electrode in accordance with the present invention, the perchloric acid salt is converted to the acid, which then acts to remove the trityl protecting group.

The reagents may also include those that are globally reactive with all of the particular sites such as those that may be added at the site and subsequently selectively converted to a reactive species as mentioned above. Exemplary of these latter reagents are phosphoramidite reagents in the presence of the salt of a weak acid such as acetic acid, tetrazole and the like. In this way the electrodes can be used to cause local acidification and, thus, activate the phosphoramidite. See, e.g., Dahl, et al., Nucleic Acids Research (1987) 15:1729–1742.

The present invention is described herein for purposes of illustration primarily with regard to the synthesis of arrays of oligonucleotides. However, the invention has application to the preparation of other molecules. The types of chemical reactions that may be carried out using the present invention include, by way of illustration and not limitation, synthesis of polymeric materials such as biomolecules, e.g., oligonucleotides and peptides, polyalcohols such as polysaccharides, e.g., carbohydrates, oligosaccharides, plastics (polyamides, polyurethanes, polyesters, polysiloxanes) and the like; conjugation of molecules such as the conjugation of reporter groups of labels to nucleic acids or nucleotides, proteins such as enzymes, antibodies, and the like; diagnostic procedures such as those involving antibody-antigen or antibody-hapten binding, nucleic acid hybridization, and so forth; molecular biological reactions such as those involving enzymes, e.g., amplification procedures such as polymerase chain reaction, ligase chain reaction, restriction enzyme reactions; and so forth. The present invention has particular application to chemical reactions involving multiple steps and a large number of compounds such as in the synthesis of combinatorial libraries and oligonucleotide and peptide arrays.

The method has particular application to the production of arrays of complex compounds such as biomolecules made by stepwise synthesis such as oligonucleotides, and the like.

Methods of oligonucleotide synthesis include phosphotriester and phosphodiester methods (Narang, et al. (1979) Meth. Enzymol 68:90) and synthesis on a support (Beaucage, et al. (1981) Tetrahedron Letters 22:1859–1862) as well as phosphoramidite techniques (Caruthers, M. H., et al., "Methods in Enzymology," Vol. 154, pp. 287–314 (1988)) and others described in "Synthesis and Applications of DNA and RNA," S. A. Narang, editor, Academic Press, New York, 1987, and the references contained therein.

In the synthesis of arrays of oligonucleotides, nucleoside monomers are generally employed. The nucleoside monomers are used to form the oligonucleotides usually by phosphate coupling, either direct phosphate coupling or coupling using a phosphate precursor such as a phosphite coupling. Such coupling thus includes the use of amidite (phosphoramidite), phosphodiester, phosphotriester, H-phosphonate, phosphite halide, and the like coupling. One preferred coupling method is the phosphoramidite coupling, which is a phosphite coupling. In using this coupling method, after the phosphite coupling is complete, the resulting phosphite is oxidized to a phosphate. Oxidation can be effected with oxygen to give phosphates or with sulfur to give phosphorothioates. The phosphoramidites are dissolved in anhydrous acetonitrile to give a solution having a given ration of amidite concentrations. The mixture of known chemically compatible monomers is reacted to a solid support, or further along, may be reacted to a growing chain of monomer units. For a more detailed discussion of the chemistry involved in the above synthetic approaches, see, for example, U.S. Pat. No. 5,436,327 at column 2, line 34, to column 4, line 36, which is incorporated herein by reference in its entirety.

The present invention also has application to the protection and deprotection steps often utilized in oligonucleotide synthesis wherein there may be several sites on a nucleoside, for example, of similar chemical nature, e.g., hydroxyl groups. The synthesis may involve blocking certain sites from reaction with protecting groups. A protecting group is one that is chemically bound to a monomer unit and which may be removed. The protecting group is attached temporarily to a potentially reactive site so as to prevent it from reacting. The protecting group assists in avoiding unwanted side reactions. The protecting groups in the present invention should be stable during the reactions involved and yet removable to yield the original site. In accordance with the present invention, attachment and removal of the protecting groups must be able to be effected electrochemically.

Phosphoramidite chemistry and solid phase oligonucleotide synthesis protocols often use a protecting group such as a dimethoxytrityl protecting group for the 5' hydroxyl of nucleosides. A phosphoramidite functionality is utilized at the 3' hydroxyl position. Phosphoramidite synthesis generally proceeds form the 3' to the 5' of the ribose or deoxyribose sugar component of he phosphoramidite nucleoside. The 5' end of the growing chain is coupled with the 3' phosphoramidite of the incoming base to form a phosphite triester intermediate. The 5' hydroxyl of the added base is often protected by a protecting group, e.g., dimethoxytrityl group, so only one new base is added to the growing chain at a time. Any unreacted 5' hydroxyls are capped off to stop the synthesis of this chain, which would be one base short at the end of the synthesis. The triester intermediate is subjected to iodine oxidation after each coupling reaction to yield a more stable phosphotriester intermediate. Without oxidation, the unstable phosphite triester linkage cleaves under the acidic conditions of subsequent synthesis steps.

Protecting groups that may be chemically bound to or removed from a support by electrochemical means may be used in the practice of this aspect of the present invention. For example, silyl protecting groups may be employed that are removable by ionic means such as with a fluoride ion. Other examples of protecting groups that may be removed electrically are those that may be removed under redox conditions. For example, methoxybenzyl and dimethoxybenzyl protecting groups are oxidatively removable (Takaku, et al., Chemistry Letters (19820 189–192).

The devices and methods of this invention allow important molecular biology and diagnostic reactions to be carried out under complete electronic control. The basic concept of this invention is a micro-electronic device with specially designed addressable microscopic locations. Each microlocation has a derivatized surface for the covalent attachment of specific binding entities. After the initial fabrication of the basic microelectronic structure, the device is able to self-direct the addressing of each specific micro-location with specific binding entities. The self-addressed device is subsequently able to actively carry out multi-step, combinatorial, and multiplex reactions at any of its microlocations. The device is able to electronically direct and control the rapid movement and concentration of analytes and reactants to or from any of its micro-locations.

In the present invention, electrochemical forces are controlled by an array of electrodes and driven by an integral integrated circuit which uses random access memory technology (RAM), so as to switch on and off the attraction of molecules such as phosphoramidite base pairs, as prescribed by a computer file, so as to build the desired compounds such as oligonucleotides.

The method of the present invention may be carried out using a device, which is brought into proximity with a reaction medium. One such device 10 is depicted in FIG. 1. A semiconductor substrate 12 has a plurality of cells 14 such as RAM cells within the semiconductor substrate 12. A plurality of digital analog converters 16 is each associated respectively with a cell 14. Each of digital analog converters 16 is respectively electrically coupled to an electrode 18, which are supported by semiconductor substrate 12. The electrical coupling is achieved by means of, for example, conventional inter-layer metallic "vias." FIG. 1 depicts optional buffer amplifier 20, which functions to isolate the digital analog converters from electrical loads applied to their electrodes. Address decoders 22 and 24 are in communication with each of cells 14 by means of, for example, conductive metallization interconnection paths. Data bus 26 is in communication with each of cells 14 by similar means. The data bus 26 delivers numerical data to each of cells 14. Also included are address buses 28 and 30, which deliver addresses to address decoders 22 and 24, respectively, and are in communication therewith by means similar to that described above for the address decoders and the data bus.

Each of cells 14 comprises storage means 32 for storing numerical data. Storage means 32 is in communication with a digital analog converter 16 in each cell 14 by means similar to that mentioned above. Storage means 32 may be similar to that known in the art such as, for example, D-type static flip-flops, a latch, a capacitor storing an analog value, and the like. The storage means may be a dynamic RAM replicator latch with a capacitor, which can store data but needs to be refreshed.

The storage means may store a value representative of a voltage or merely the fact that a cell was selected and electrode is more or less switched to an analog bus. Both situations are exemplified by D-type flip-flops in conjunction with a digital bus.

In a preferred embodiment, data such as numerical data is sent to storage means 32 of each of cells 14 by means of the data bus. The numerical data is representative of an electric signal as explained in more detail below. Addresses are sent to address decoders 22 and 24 whereby the numerical data is stored in the storage means and electric signals are selectively applied to each of the electrodes by means of digital analog converters 16. A chemical reaction takes place proximal to and in response to the field at the electrodes.

The numerical data may be, for example, binary numerical data; in a simple case representative of values 0 volts and 3 volts, and so forth. In the latter case the data are represented by a single bit, 0 or 1 ("0"→0 volts and "1"→3 volts).

The devices used in the present invention may be fabricated according to procedures well-known to those skilled in the art of digital and IC design. Reference books that are exemplary of those directed to the above include VLSI Technology by S. M. Sze (1988) ISBN 0-07-062735-5 and Basic VLSI Design by Pucknell and Eshraghian (1988) ISBN 0 7248 0105 7. Typical integrated circuits use form two to five or more layers of interconnection metal with insulator layers in between. Modern IC's usually use an aluminum alloy for metallization in conjunction with "vias" of a tungsten alloy. The metal layers are generally of a thickness on the order of approximately about 0.1 to about 1 micron.

Figure 2:
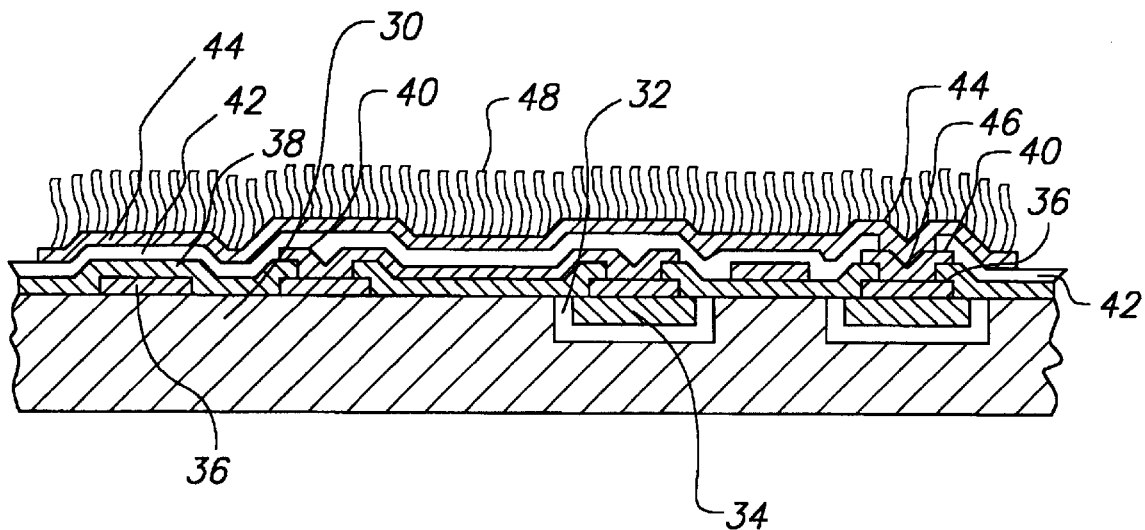
FIG. 2 is a schematic diagram depicting an aspect of a device in accordance with the present invention.

FIG. 2 depicts, in cross-section, a portion of a device in accordance with the present invention showing an electrode assembly. P-substrate 30 contains depletion regions 32 and N-diffusion regions 34. Metal layer 36 is formed from a metal and is found within insulator layer 38. Above 36 lies metal layer 40, which is found within insulator layer 42. The upper most layer 44 is also formed from a metal and is the outer layer of the electrode and has oligonucleotides 48 attached thereto. Via 46 is formed by the interconnection of 36, 40, and 44, which may be referred to as metallization layers. In some systems, it may be desirable that the surface of the electrode be flat. In this circumstance, the circuitry may be fabricated so as to lie between the electrodes and not underlying them as shown in FIG. 2.

Gold may be employed for one or more metallization layers. For cost reasons in the present invention aluminum is preferred for the intermediate metal layers and gold for the top layer, which would be the electrodes. Fixed electrodes may be plated over by processes well-known in the art of IC, with a variety of metals, including gold and nickel, chosen to be the most compatible with the oligomer primer attachment chemistry. In addition to aluminum, suitable metals for circuitry include gold, tin, platinum, palladium, and various metal combinations.

The insulator layers are usually of a thickness similar to that mentioned above for the metallization layers and are made of an insulating material, i.e., a non-conductive material such as silicon dioxide and the like. The insulator layers are grown above and intrinsically adhered to the metal layers. The overcoat layer is conveniently applied by deposition techniques, e.g., plasma enhanced chemical vapor deposition, and the like.

The connections between the electrodes and the circuit cells are provided by the interconnected layers of metal and insulator by means of holes in the insulator. See, for example, the depiction of via 46 in FIG. 2. These holes are typically on the order of fractions of microns, usually about 0.2 to about 2 microns in diameter and may be formed by microlithographic or other techniques well-known in the art of IC design such as electron beam lithography, ion beam lithography, or molecular beam epitaxy. While microscopic locations sites are desirable for some applications such as high density arrays, larger addressable sites (e.g., larger than 2 mm) may be employed for preparative scale synthesis.

The electrodes may be either left exposed or, alternatively, they may be over-coated with an insulator such as $SiO_2$. In the former case, with an aqueous conductive analysis environment, current flow will take place together with electrochemical reactions. Either the exposed electrodes or $SiO_2$ over-coated electrodes are amenable to an organic non-conductive chemistry in which mobility is effected by the action of a simple electrostatic field.

After the sites have been created, chemical techniques are used to provide for specialized attachment of chemical reagents. In this way, for example, the electrodes at the respective sites may affect or cause the free field electrophoretic transport of specific electrically responsive chemical reagents to a specified location where the chemical reagent may attach to the chemical entity at the particular site. The procedure for creating the attachment chemistry is sometimes referred to a "priming" the surface. To this end, the top surface of the electrodes, either the metal electrode layer itself or an insulator layer, is next modified so as to prepare the surface for attachment of the monomeric building blocks in accordance with the present invention. This surface may be the metal surface itself or an overcoat layer as mentioned above. It is an advantage of the present invention that the entire surface of the IC may be coated with the necessary modification keeping in mind that the underlying electrodes must not be prevented from functioning. The surface may be modified with groups or coupling agents to covalently link the initial nucleoside to the surface at the site of application of the electric field. Representative groups include, by way of illustration and not limitation, amino, especially primary amino, hydroxyl, thiol, sulfonic acid, phosphorous and phosphoric acid, particularly in the form of acid halides, especially chloride and bromide, and carboxyl, and the like. The reactive groups are conveniently attached to the surface commonly through a hydrocarbyl radical such as an alkylene or phenylene divalent radical. Such hydrocarbyl groups may contain up to 10 carbon atoms.

One preferred procedure for the derivatization of the metal electrode surface uses and aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or hydroxyl groups on metal and silicon surfaces. APS provides primary amine groups for the subsequent covalent coupling reactions of the oligonucleotide synthesis. Such a procedure is described in EP 0 173 356 B1, the relevant portions of which are incorporated herein by reference. While this represents one of the preferred approaches, a variety of other attachment reactions are possible for both the covalent and non-covalent attachment as mentioned above.

Other considerations for the design and fabrication of a device include, but are not limited to, materials compatibilities, nature of the reagents and the subsequent reactants and analytes, and the number of reaction sites at which the electrodes are located.

The electrodes of the array are at predetermined locations or sites on the integrated circuit chip and generally are of the micro scale. The usual function of the electrode is to apply a DC signal. By functioning to apply a DC signal is meant that a electrode is biased either positively or negatively, operating in a direct current mode, which can affect or cause the electrically induced movement of a molecule to the electrode. It should be noted that other types of signal application may be used. For example, the signal may be an AC signal, which might be useful to cause local agitation or scrubbing at the surface. This local scrubbing may have an advantage in providing for enhanced speed of binding. The AC signal may be applied to selected at selected sites by generation of AC signal at the selected sites. On the other hand, one or more tree-like signal buses that are accessible to each and every site may be used. To each bus may be applied either or both an AC or a DC signal. Each addressed site may, as desired, connect any signal bus to its electrode in response to appropriate settings of its storage element.

While the term "electrode" is used herein, it should be noted that it is an electric field generated in the area of the addressable site that is responsible for attracting the electrically responsive species to the site. Typically, such an electric field is generated between two oppositely charged conducting surfaces such as plates. In other words one needs both an electrode and a counter-electrode to generate the electric field. There are several approaches. In one approach, the counter-electrode may be a surface above, and parallel, to the array of electrodes. In another approach, a grid of vertical and horizontal metallization in the form of "streets" such as, for example, gold metallization may lie between electrodes, which may be considered as "parks" in this analogy. The grid may be at ground or at some potential other than that of the electrode. In yet another approach, electrodes other than those actually activated at any particular point in time can be used as counter-electrodes. Since, in general, only about one-fourth of the sites are made attractive at one time, the remaining sites will be repulsive and may be set at a voltage that functionally will act as a counter-electrode.

A device can be designed to have as few as two addressable sites or as many as hundreds of thousands of sites. The addressable sites may be of any shape, preferably, square or rectangular for maximizing their area. The size of a site can be varied and can be of any size, usually in the range from about 2 microns to about 2 millimeters, preferably, in the range of about 5 to about 500 microns.

In the present invention protection or blocking agents that are responsive to electric fields such as described above may be activated or deactivated, e.g., to protect or deprotect particular chemical groups. By selectively applying electric fields to the desired positions known polymers may be synthesized at positionally defined regions on the present device.

Figure 3:
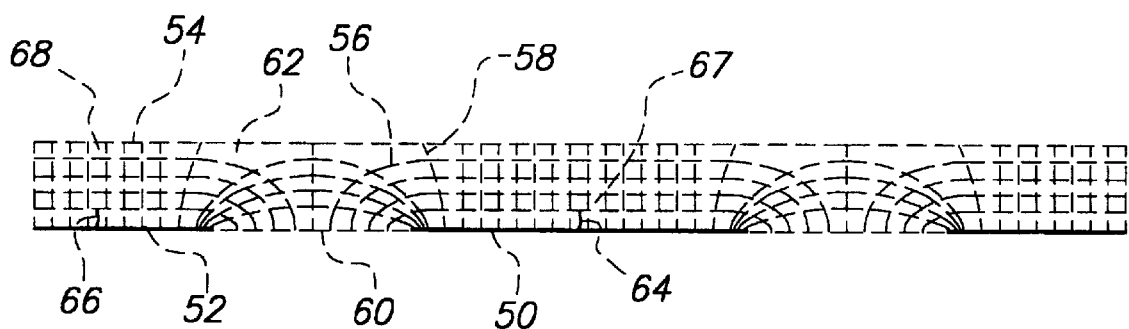
FIG. 3 is a schematic diagram depicting an aspect of a device in accordance with the present invention.

In one embodiment of the present invention, by way of illustration and not limitation, there is employed a 4-millimeter square rectilinear array of 16,000 electrodes. Each electrode is 30 microns square, although electrodes of ten times this density are readily achievable. Underlying each electrode is a RAM cell, with a simple digital analog converter, capable of setting a voltage on the electrode, typically between 0 and 5 volts. The excess space under the electrode allows space for redundant error correcting electronics. An example of the above is shown in FIG. 3. Electrode 50 may be set at, for example, +5 V. Electrode 52 is set at −5 V and is adjacent to electrode 50. Counter electrode 54 is set at 0 V. The electric field that is generated includes equipotential line 56, which may be at +1 V. Also shown is field line 58, which may be, e.g., the path of a charged ion. As a general rule 56 and 58 are perpendicular to each other everywhere. Also depicted in FIG. 3 is insulative surface 60 and reaction medium 62. Oligonucleotides under synthesis are shown as 64 and 66, respectively. In the embodiment illustrated in FIG. 3, a reagent 67 is being attracted to activated electrode 50, where it will react with the growing oligonucleotide 64. Reagent 68 is also shown in the vicinity of electrode 52, which has not been activated. Thus, reagent 68 is not attracted to electrode 52.

The array chip is addressed by a 16-bit wide bus, of which 14 lines contain the binary address of each electrode, and two lines program one of four voltages. Chemical reactions such as oligonucleotide synthesis are conducted at the wafer level before the chips are diced out. In this manner, a 6-inch wafer containing over one thousand die may be economically fabricated as a single batch. The silicon process chosen may be one that is well-known in the art such as CMOS and the like. The oligonucleotide probes are built upon the sites defined by the electrodes. The sites are first primed, either selectively, or simply as a part of the whole surface. The priming is carried out by means discussed above. Another approach uses "spin-on" fluidic techniques well-known in the IC industry.

The fabrication "tank" consists of a flow through system as depicted in FIG. 3, in which a reference electrode is placed parallel to the wafer, and means are provided for electronically programming the voltages on the site electrodes. Typically, it is desired that the electrodes be driven to voltages either a few volts above or below the voltage on the reference electrode. This is most readily implemented by placing an intermediate potential on the reference electrode, such as +2.5 V, and then programming the site electrodes electronically to a voltage either above or below this value; i.e., to 0 or +5 volts, or to +1.5 V or +3 volts.

Means are provided to selectively introduce one of the four electrically responsive A, T. G. or C nucleoside reagents, e.g., phosphoramidites, in solution into the space between the reference electrode and the wafer. The appropriate solution may be flowed through from the side or introduced through means of making the reference electrode porous.

The process of synthesizing oligonucleotides in accordance with the present invention comprises repeatedly exposing the array to solutions containing sequentially the A, T. G. and C phosphoramidites, for example, in the presence of attractive or repulsive fields at each site. Since the phosphoramidites are positively charged, a negative potential at the site attracts the molecule, while a positive one repels it. Because of the small size and high mobility of the molecules, the time required for application of the voltage is short of the order of a second. Once the phosphoramidites are drawn into the vicinity of the oligonucleotides under construction, the attachment reaction is virtually instantaneous.

In an alternate embodiment a solution containing phosphoramidite reagents may be sequestered in a gel or a semi-permeable membrane. The gel or membrane may be brought into contact with the array and electric potential may be employed to attract down the reagent by electrophoretic movement to the particular electrodes that are electrically activated.

The following discussion will ignore the intermediate chemical steps as mentioned above that occur between each attachment cycle. Thus, to start the oligonucleotide probe building process, all sites to which an "A" nucleotide is to be added are programmed negative with respect to the reference electrode, while the rest are programmed positive. The process is repeated sequentially for the continued synthesis of the desired oligonucleotides selecting the appropriate A, T, G and C nucleotides. In this manner, oligonucleotides of, for example, length 20 nucleotides are fabricated in at most 80 chemical cycles. In this particular embodiment, at completion approximately 16 million oligonucleotides are synthesized at respective sites upon the six-inch wafer, which may be scribed and broken into 1000 or more chips. These chips, once dried, are now complete. Further electrical connections to the chips are not normally necessary unless some other operation such as electroosmotic pumping of polynucleotide analyte across the chip is anticipated.

Thus, as can be seen from the above description, the present invention allows for the fabrication of hundreds or thousands of devices in parallel. In use, tan entire wafer containing on the order of a thousand devices is communicated with be a common programming source, which accesses all or groups of the chips on the wafer. The wafer is exposed chemically by dipping or, preferably, by spinning, both of which are similar to well-known processes in the IC processing industry. The wafer is placed on a rotatable platen in a powered state, which is unlike the approach used in IC processing. Connection to the platen is by means of a set of slip rings. Electronic states are set up and chemicals such as reagents for carrying out a chemical synthesis are applied to the spinning disc with centrifugal force used to spread and void the chemicals. Following the chemical syntheses the wafer may be diced into the appropriate number of chips desired.

The above fabrication may include provisions for reducing electrical noise often present when data is fed through slip rings. In one approach this is accomplished by redundant brushes. Alternately, power, e.g., from a battery, and non-volatile data storage may be included in the rotating assembly such that the data may be transferred before rotation is commenced. The wafer may be divided into sections such that a number of different chemical patterns may be manufactured in a run of only one wafer. For example, a 512-die wafer could be configured to include sixteen addressable section of 32 die each. In principle, the subdivision could be carried as far as desired with every individual die being individually programmable. In this example, when programmed with a parallel data bus, 23 address lines might be employed, 9 for chip address and 14 to address 16,000 sites on each die. In this instance, for fabrication of DNA on the chips, 2^21 or approximately 2 million sites would be turned on for each chemical step. At a 1 MHz clock rate, this should take only two seconds. Other additional features may include provisions for avoiding wafer-scale disfunctions, relaxed interconnect-metallization rules, decoupling at each "geographical area, self-testing provisions such as write verification, and so forth.

The oligonucleotide arrays may be used to carry out nucleic acid hybridization in a diagnostic fashion. To this end the array is exposed to a solution containing the polynucleotide analytes in the usual manner and labeled DNA fragments selectively hybridize at sites where a complementary oligonucleotide is found. Since the chips are opaque, they are read from one side; either dry, or in solution.

FIG. 1 shows an array chip diced from a six-inch wafer of silicon. For clarity and purposes of discussion, only 16 of 16,384 elements are shown. This should not be viewed as limiting the present invention.

The number of oligonucleotides synthesized on the device as well as the size of each site of oligonucleotide synthesis are governed by number of factors such as the nature and amount of the analyte, the desired level of sensitivity, cost, chip yield, and the like. Generally, an upper limit is the comparable RAM chip density. The number of sites may be from about 2 to about 16 million, usually about 100 to about 100,000 and the size of each site maybe from about 5 microns to about 1 mm, usually, about 20 to about 200 microns. Generally, larger sites mean greater sensitivity but possibly greater requirements for sample volume. If relatively few sites are needed, and sample is plentiful, then the individual sites can be made up to 1 mm square. Circuit density ceases to be an issue. Various approaches may be used for processing the wafer such as known processing techniques as applied to a 6-inch wafer such as those described in Sze, supra. If an acceptable cell size may be relatively large, for example, 50 micron square, then an inexpensive older IC process may be used. Alternatively, other low cost per unit area processes may be used such as those common to manufacturing large active matrix LCD displays.

On the other hand, it may be desirable to maximize the number of sites to one million or more. In this embodiment, it is desirable to employ relatively small 5 to 10 micron square sites and to use fine-line IC processes known in the art such as CMOS processes, e.g., CMOS-14, bipolar processes, MOS processes, NMOS processes, ECL and so forth. Such processes are more expensive than those described above with respect to relatively low-density arrays of oligonucleotides.

An example of an intermediate-to-dense involves electronics under each electrode have a complexity of the order of 20 transistors. A reasonably dense IC process in CMOS is one producing metal lines at a pitch of 1 micron, using 0.35 $\mu$ details. Such a process replicates the complexity required at each element in a square approximately 12 microns on a side. One embodiment using this process features approximately 256,000 sites on a square chip 6 mm on a side. Processing costs in this approach are reasonable with a yield of approximately 500 devices.

The chips may be chemically processed while they are in either the chip state or the wafer state. Chip-state processing is the simplest. Briefly, the chip is mounted in a suitable package, such as to a conventional IC package. It is then connected to a programming source and chemically processed. Alternatively, wafer-scale processing may be used wherein the entire wafer of parallel chips is processed at the same time. Because currents and speeds are low in this latter approach, it is only the chance of shorts on major interconnecting buses that place a practical limit on the number of devices that may be processed at one time. Employing looser design rules for these interconnecting paths minimizes the likelihood of such shorts.

The operation of the chip is best understood by considering the case where the chips are processed individually. Referring now to FIG. 1, less than 20 electrical connections to the chip are required for a 16,384-element embodiment. Fourteen lines are required for address, 2 for data, and a few more for power and ground. The 14 address lines carry logic signals representing 2614 or 16,384 states. Since the array is most advantageously made square, 7 lines are dedicated to encoding the x-address and 7 lines are dedicated to encoding the y-address. These 7 lines are fed each to the x-address decoder and the y-address decoder.

The 7 address lines connected to each decoder can represent $2^7$ or 128 states. The output of each decoder is 128 lines. Only one output line is active at a time, namely, the one representing the state of the 7 address lines. For example, a 14-bit address sent to the chip with value of 00000000000010 has a decimal value of 2. Splitting the address into two seven-bit bytes, an address of 0000010 would be sent to the x-axis decoder and an address of 0000000 would be sent to the y-axis decoder. The 0000000 sent to the y-axis decoder causes the first or lowest of its 128 output lines to become active. Accordingly, the line might be set "high", while the remaining 127 lines would be set "low," which means that the line is set to a voltage of zero. The 0000010 address, a binary "2", is the third ascending state that can be represented and, thus, causes the third line of the x-axis decoder to be set active (or "high"). In this way a positive ion such as a nucleotide phosphoramidite is attracted to the electrode governed by this cell.

FIG. 1 may be visualized as representing the lower-leftmost 16-element corner of the 16,384-element array. The nearest element has address 00000000000000; the rightmost, 00000000000011; the leftmost, 00000110000000; and the uppermost, 00000110000011.

The 128 decoded address lines from each decoder form a grid on the chip. At each intersection is a cell of circuitry and an electrode. Each cell is only addressed when both its x and y decoded address lines are active. Thus, for any applied 14-bit address, only one cell is addressed at a time.

In this embodiment, two data lines enter the chip. They are capable of representing $2^2$ or 4 logic states. These will ultimately produce one of four possible voltages on whichever electrode in the array happens to be addressed. More specifically, when a circuit cell is addressed, it latches the data from the data lines by means of two D-type flip-flops. This data is held, or latched, while the process proceeds to latch independent data into each of the other 16,383 cells. The state latched into each circuit cell may have a value of 00, 01, 10 or 11. The latching is static, as opposed to dynamic, for simplicity. The operation is reminiscent of the behavior of computer random-access-memory "RAM" chips. The preferred mode of operation is as a static RAM, which means that data does not need to be periodically refreshable by read/write cycles. However, this is not a requirement. The byte length is two bits.

The state latched into each circuit cell is delivered to a digital-to-analog converter (DAC) for conversion to an analog voltage (for example, 0, 1, 2, or 3 volts). This output is shown buffered by a unity-gain amplifier. However, drive requirements for the electrode are so small that the amplifier may be incorporated as a functional part of the DAC itself and, in that sense, eliminated.

A beneficial feature not shown in this drawing is means to electrically test the device before the chemical cycles commence. This is easily accomplished by adding an additional line exiting the chip, which is connected in parallel to every array circuit cell. Each cell has an analog switch, which allows sequential connecting of its analog output voltages to the bus when the cell is addressed. The test and verification cycle is as follows: Each cell is written to four times, once with each of its four allowable 00, 01, 10 and 11 states. After each write, the analog bus is monitored for presence of the correct voltage.

The size of the array may be varied depending on the application as discussed above. Fewer or more elements may be employed, depending on cost considerations, the size of the sample available for analysis and the size of the electrodes necessary to obtain the required sensitivity.

Greater or fewer voltage states may be provided for on each electrode as well as voltages of both polarities. In this regard the voltages may be from any value between the two positive and negative extremes of supply voltages available to the chip. The particular voltages selected will depend on the application in which the device is used. The voltage range does not need to be represented in equal steps; for example, four binary states could be assigned values of 0, 0.5, 4.5, and 5.0 volts.

In its simplest form only two voltage levels are provided. In this approach most of the complexity of the cell vanishes and a one-bit latch is all that is required. In this form, the density of an array can be increased considerably.

The spacing between sites on the device is determined by the ease of fabrication, the requirement for resolution between the various sites, and the number of sites desired on a device. However, particular spacing between sites or special arrangement or geometry of the sites is not necessary for device function. Any combination of micro-locations (i.e., underlying electrodes) can operate over the complete device area. Nor is it necessary to enclose the device or confine the sites with dielectric boundaries. The device functions by attaching molecules such as specific binding molecules, chemical and analytical reagents to the surface of an addressable site adjacent an electric field that is selectively generated.

In addition to the above-mentioned features, the device may also comprise identification codes, which may be either visual or electronic, to provide for interrogation of features of the device.

In one embodiment of the present invention, a plurality of analog buses is employed and the item of numerical data identifies which analog bus connects to the electrode. In this embodiment each site may be switched to one of the plurality of analog buses. For efficiency of operation it is desirable to be able to set sites to one of perhaps two voltages, i.e., to either attract or repel chemical species. This may be accomplished in the present invention by traversing the chip with several analog buses such as, for example, two analog buses, namely, Bus A and Bus B. Bus A might be set to 1 V and Bus B might be set to 3 V and the grid set to 2 V. The grid voltage may be set by employing an on-chip DAC or by an external lead. For the sake of illustration the setting at 1 V repels a chemical species while the setting at 3 V attracts chemical species and the setting at 2 V does neither. A digital value is written to each cell of 0, 1 or 2 (in binary 00, 01, 10) indicative of whether to connect the cells electrode by means of a switch to Bus A, Bus B or to the grid. More specifically, if the data "00" is sent to a cell, then its switch is set to connect that cell electrode to Bus A, to which we are holding at 1 V, by an on-chip or especially an off-chip source. On the other hand, if the data "01" is sent to a cell, then its switch is set to connect its electrode to the grid. This grid is in essence a third bus since it is proximal to all cells. The difference is that it is an electrode that is not insulated but is in proximity to or in contact with the reaction medium. The above approach requires neither the complexity of the analog non-volatile storage mechanism nor the need to periodically refresh the cell. Thus, the present invention offers advantages over the known methods such as the biological electrode array described above wherein each electrode in the array is coupled to a respective sample-and-hold circuit. It should be noted that one or more of the analog buses could optionally be the system ground or other supply voltage since these are merely voltages bused to each and every cell.

Figure 4:
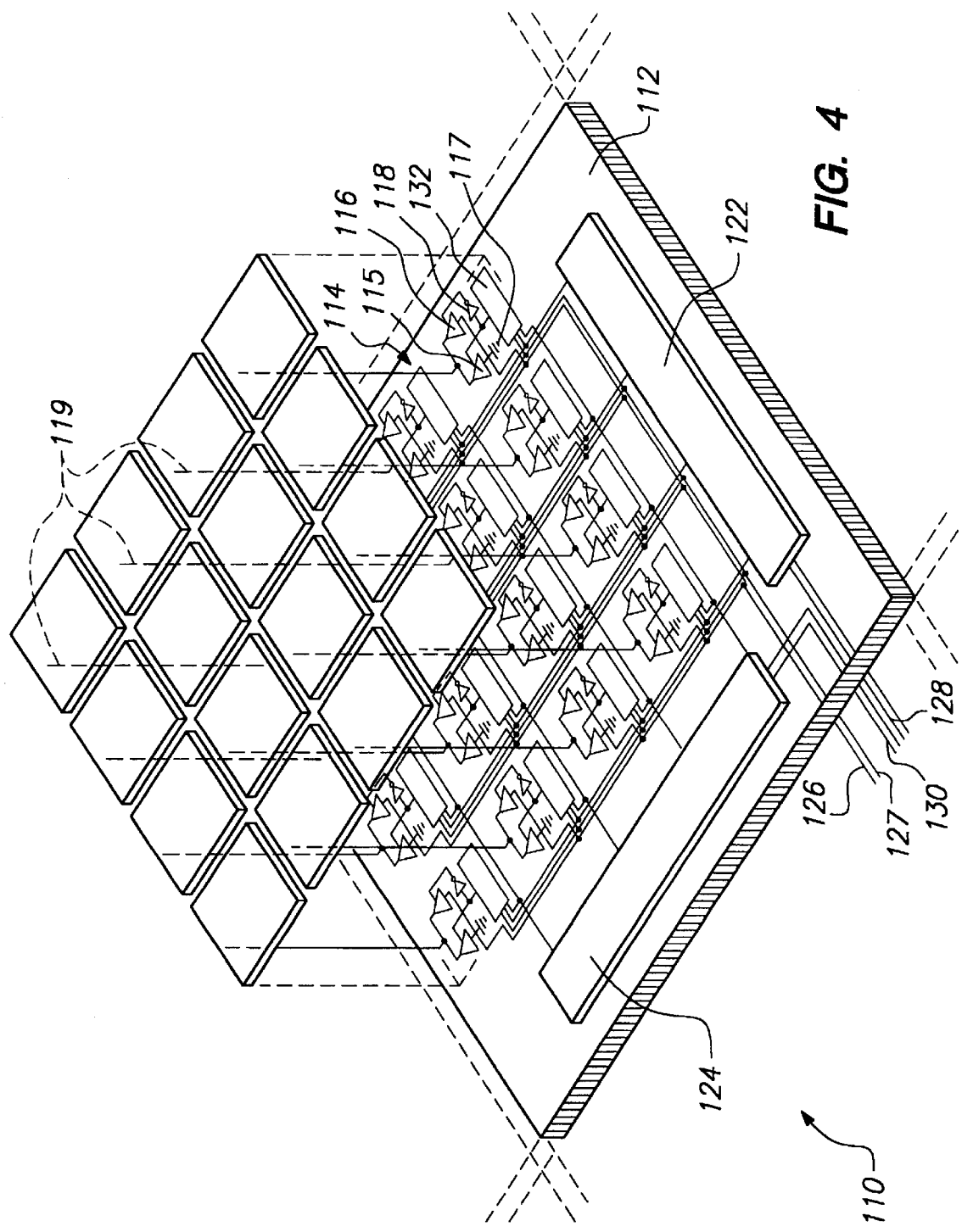
FIG. 4 is a schematic diagram depicting an alternate device in accordance with the present invention.

Another device (110) in accordance with the present invention is depicted in FIG. 4. A semiconductor substrate 112 has a plurality of cells 114 such as RAM cells within the semiconductor substrate 112. Each of the cells 114 has analog switches 115 and 116. Switch 115 is electronically coupled to ground 117, which may be viewed as a first analog bus, and switch 115 connects this first analog bus to electrode 119. Switch 116 is electronically coupled to a second analog bus 126 and switch 116 is electronically actuated by inverter 118, which connects this analog bus 126 to electrode 119. The electrodes 119 are supported by semiconductor substrate 112. The electrical coupling is achieved by means of, for example, conventional inter-layer metallic "vias" as mentioned above with respect to device 10 of FIG. 1. Address decoders 122 and 124 (FIG. 4) are in communication with each of cells 114 by means of, for example, conductive metallization interconnection paths. Analog bus 126 as well as data bus 127 is in communication with each of cells 114 by similar means. The data bus 126 delivers numerical data to each of cells 114. Also included are address buses 128 and 130, which deliver addresses to address decoders 122 and 124, respectively, and are in communication therewith by means similar to that described above for the address decoders and the data bus. Each of cells 114 comprises storage means 132 for storing numerical data. Storage means 132 is in communication with inverter 118 in each cell 114 by means similar to that mentioned above.

The embodiment of the present invention depicted in FIG. 4 is one in which electrical signals are communicated to each of the sites by means of selectively switching them to an analog bus. As with device 10 of FIG. 1, device 110 is a 16-site representation of a much larger chip. In the embodiment of FIG. 4, only a single-wire bus is employed. Each site is capable of being electrically connected to one of two signals. The first signal is zero volts, as derived by switching the site to the system ground 117 by means of switch 115. Thus, in this example, the system ground becomes the bus A of the previous example. The second signal is whatever signal is applied to the analog bus 126 (bus B).

The second signal may be variously obtained form, for example, an on-chip DAC, or, as shown, from an off-chip source, which optionally may be buffered on the chip. The signal is typically DC, such as, for example, 3 volts; however, any DC or AC signal may be applied.

In use, either a 0 or a 1 is written to storage means 132 at each site. The value appears on the line labeled "data," which is accessible to every site, and written to each site in turn as each site is addressed, via the 14 address lines (4 of which are shown in FIG. 4 as 128 and 130). The output of this storage means 132 or latch is used to enable either one of the two analog switches 115 and 116 shown (the /E line (not enable) feeding the two switches). Switch 115 is enabled directly from storage means 132, while switch 116 as shown is enabled by the inverted output of storage means 132. Switches 115 and 116 are shown being activated by a logic low signal.

To further understand this embodiment assume that a voltage of +3 volts is applied to the analog bus and system ground is at zero volts. If a logical "0" is written to a particular storage means, then the storage means 132 will in turn enable the switch 115, thus connecting the electrode 119 for that site to system ground 117 or zero volts. Conversely, if a logical "1" is written to the storage means 132, then it in turn will enable switch 116 and connect the electrode 119 at that site to the signal bus, which in this embodiment is +3 volts. Thus, it is seen that a potential of either 0 or 3 volts may be applied to each of the electrodes.

In an alternative embodiment of the above, additional bus signals may be routed to the chip or the supply itself may be employed.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for carrying out multiple chemical reactions, said method comprising:
    (a) bringing a plurality of electrodes supported by a semiconductor substrate into proximity with a reaction medium, said reaction medium comprising reagents for carrying out said chemical reactions,
    (b) sending an item of numerical data to storage means in each of a plurality of cells within said semiconductor substrate by means of a data bus, said item of numerical data participating in the selection of a voltage to be applied to said electrodes, and
    (c) sending an address to address decoders in communication with said storage means, whereby said item of numerical data is stored in said storage means and electric signals are selectively applied to each of said electrodes by means of a plurality of digital analog converters, each electrically coupled to a respective electrode and each being present on said semiconductor substrate and associated with a respective cell and whereby a chemical reaction takes place proximal to and in response to the field at said electrodes to which said electric signals are selectively applied.

2. The method of claim 1 wherein said item of numerical data is binary numerical data.

3. The method of claim 1 wherein said item of numerical data is one bit in length and wherein said digital analog converters are integral with said storage means.

4. The method of claim 1 wherein an insulative layer covers said plurality of electrodes.

5. The method of claim 4 wherein said insulative layer is removable from said semiconductor substrate.

6. The method of claim 1 wherein said reagents are responsive to electric fields.

7. The method of claim 1 wherein said reagents are reagents for carrying out synthesis of polynucleotides.

8. The method of claim 5 wherein said reagents are nucleoside phosphoramidites or nucleoside phosphonates.

9. The method of claim 1 wherein an array of oligonucleotides is synthesized on a surface of said semiconductor substrate.

10. The method of claim 9 wherein from about $10^2$ to about $10^8$ different oligonucleotides are synthesized, each in an area of from about 2 micron by 2 micron to about 500 by 500 micron.

11. The method of claim 9 wherein said oligonucleotides are about 10 to 30 nucleotides in length.

12. The method of claim 1 wherein said chemical reaction comprises selectively generating a reactive species at said electrodes.

13. The method of claim 1 wherein said chemical reaction comprises deprotecting a molecule at said electrode.

14. The method of claim 1 wherein said medium is a non-aqueous medium.

15. The method of claim 1 wherein said item of numerical data is representative of an electric signal.

16. A method for carrying out multiple chemical reactions, said method comprising:
    (a) bringing a device into proximity with a reaction medium, said reaction medium comprising reagents for carrying out said chemical reactions, said device comprising (i) a semiconductor substrate, (ii) a plurality of electrodes supported by said semiconductor substrate, (iii) a plurality of cells within said semiconductor substrate, (iv) a plurality of digital analog converters, each electrically coupled to a respective electrode and each being present on said semiconductor substrate and associated with a respective cell, (v) address decoders in communication with each of said cells, (vi) a data bus for delivering binary numerical data to each of said cells, (vii) address buses for delivering addresses to said address decoders, and (viii) storage means in each of said cells for storing said numerical data, said storage means being in communication with said digital analog converter in said cell,
    (b) sending binary numerical data to said storage means of each of said cells by means of said data bus, said binary numerical data being representative of an electric signal, and
    (c) sending addresses to said address decoders whereby said binary numerical data is stored in said storage means and electric signals are selectively applied to each of said electrodes by means of said digital analog converters and a chemical reaction takes place proximal to and in response to the field at said electrodes.

17. The method of claim 16 wherein said reagents are reagents for carrying out synthesis of oligonucleotides.

18. A device comprising:
    (a) a semiconductor substrate,
    (b) at least one surface for carrying out chemical reactions,
    (c) a plurality of electrodes supported by said semiconductor substrate,
    (d) a plurality of cells within said semiconductor substrate,
    (e) a plurality of digital analog converters, each electrically coupled to a respective electrode and each being present on said semiconductor substrate and associated with a respective cell,
    (f) address decoders in communication with each of said cells,
    (g) a data bus for delivering an item of numerical data to each of said cells,
    (h) address buses for delivering addresses to said address decoders, and
    (i) storage means in each of said cells for storing said item of numerical data, said storage means being in communication with said digital analog converter in said cell.

19. The device of claim 18 wherein said data bus is for delivering binary numerical data.

20. The device of claim 18 further comprising an insulative layer covering said device at least at said plurality of electrodes.

21. The device of claim 18 wherein said insulative layer is removable.

22. The device of claim 18 comprising from about $10^2$ to about $10^8$ different cells, each in an area of from about 2 micron by 2 micron to about 500 by 500 micron.

23. The device of claim 18 further comprising means to electrically test the device before use.

24. A chip for electronically addressing a matrix of sites, each site to which may be directed a chemical reaction; said chip comprising:

(a) a semiconductor substrate;

(b) a matrix of electronic circuit cells fabricated within said semiconductor substrate, (c) address decoders for activating a cell in response to an address applied to said chip;

(d) a data bus for delivering binary numerical data to said cells;

(e) storage means in each of said cells for storing binary numerical data from the data bus when activated by addresses decoded by said address decoders, (f) digital to-analog conversion means in each cell for converting binary numerical data into an electrical signal;

(g) an electrode plate connected to each of said digital-to-analog conversion means, wherein electrical signals representative of said binary numerical data are selectively applied to each of said electrode plates for the purpose of inducing, when the device is placed proximal to a chemical medium, selective chemical activity according to the binary numerical data provided.

25. A method for carrying out multiple chemical reactions, said method comprising:

(a) bringing a plurality of electrodes supported by a semiconductor substrate into proximity with a reaction medium, said reaction medium comprising reagents for carrying out said chemical reactions, (b) sending an item of numerical data to storage means in each of a plurality of cells within said semiconductor substrate by means of a data bus, said item of numerical data being representative of an electric signal, and (c) sending an address to address decoders in communication with said storage means, whereby said item of numerical data is stored in said storage means and electric signals are selectively applied to each of said electrodes by means of a plurality of digital analog converters, each electrically coupled to a respective electrode and each being present on said semiconductor substrate and associated with a respective cell, and whereby a chemical moiety proximal to said electrode is selectively activated for reaction with a reagent in said reaction medium, said selective activation being in response to the field at said electrodes to which said electric signals are selectively applied.

26. The method of claim 25 wherein said chemical moiety is a reagent for oligonucleotide synthesis.

* * * * *